United States Patent [19]
Ransberger et al.

[11] Patent Number: 5,505,942
[45] Date of Patent: Apr. 9, 1996

[54] USE OF HYDROLYTIC ENZYMES FOR THE PROPHYLAXIS OF SPONTANEOUS ABORTION IN PREGNANT WOMEN WITH HABITUAL IDIOPATHIC ABORTION IN THEIR ANAMNESES

[75] Inventors: Karl Ransberger, Seeshaupt; Friedrich-Wilhelm Dittmar, Söcking; Rudolf Kunze, Berlin; Gerhard Stauder, Wolfratshausen, all of Germany

[73] Assignee: Mucos Pharma GmbH & Co., Germany

[21] Appl. No.: 328,289

[22] Filed: Oct. 21, 1994

[30] Foreign Application Priority Data

Oct. 25, 1993 [DE] Germany .............. 43 36 343.1

[51] Int. Cl.⁶ .............. A61K 38/43; A61K 38/00; A61K 31/70; A61K 31/715
[52] U.S. Cl. .............. 424/94.1; 514/21; 514/25; 514/53; 514/177; 514/179; 514/182
[58] Field of Search .............. 424/94.1; 514/21, 514/25, 53, 177, 179, 182

[56] References Cited

U.S. PATENT DOCUMENTS 5,140,100  8/1992  Braunstein et al. .............. 530/300
5,276,017  1/1994  Feinberg et al. .............. 514/21

OTHER PUBLICATIONS

Chemical Abstracts, vol. 88, No. 19 issued 19 May 1978, Stepanova et al., "Some indexes of the adrenal cortex function in children whose mothers were treated with steriod hormones during pregnancy for habitual miscarriage" see p. 85, column 2, abstract No. 131344e, Vopr. Okhr. Materin. Det., 22(9), 34–5.

Chemical Abstracts, vol. 98, No. 7 issued 25 Feb. 1983, Kitagawa et al., "Prevention of habitual abortion in cows with 17–α–hydroxyprogesterone caproate and progesterone level in milk" see p. 93, column 2 and 94, column 1, abstract No. 47132h, Nippon Juishikai Zasshi, 35(7), 398–401.

*Primary Examiner*—Marianne M. Cintins
*Assistant Examiner*—Kevin E. Weddington
*Attorney, Agent, or Firm*—Scully, Scott, Murphy & Presser

[57] ABSTRACT

The present invention relates to the use of hydrolytic enzymes for the prophylaxis of spontaneous abortion in pregnant women in need thereof with habitual idiophathic abortion in their anamneses.

14 Claims, No Drawings

USE OF HYDROLYTIC ENZYMES FOR THE PROPHYLAXIS OF SPONTANEOUS ABORTION IN PREGNANT WOMEN WITH HABITUAL IDIOPATHIC ABORTION IN THEIR ANAMNESES

DESCRIPTION

The present invention relates to the use of at least one hydrolytic enzyme for the prophylaxis of abortion in pregnant women with habitual idiopathic abortion in their anamneses.

One talks about habitual abortion when at least three successive pregnancies end before the 28th gestational week with spontaneous abortion. (Pschyrembel, Klinisches Wörterbuch, 255th ed., Walter de Gruyter, 1986). Habitual spontaneous abortions are sometimes due to anatomic, genetic or hormonal anomalies of the patients concerned. Examples thereof are congenital uterine anomalies, chromosomal abnormalities, thyroid dysfunctions, diabetes mellitus, autoimmune diseases, viral or bacterial infections, etc. (Makino, T. et al., Annals New York Academy of Sciences, pp. 597–604, 1990). At an incidence of 0.4%, however, this kind of abortion is idiopathic, i.e., of unknown cause (disposition).

Therapeutic or prophylactic measures which have so far been taken to maintain pregnancy in case of pending abortion without any hints at a possible cause are cervical cerclage, hormone supplementation (estrogen, gestagen, progesterone, etc.) and the administration of allogenic leukocytes and polyvalent immunoglobulins.

The prophylaxis of habitual abortion with combinatory preparations based on hormones leads, according to experience, to normal birth only in every tenth pregnant woman.

Higher success rates in cases of habitual abortion have been achieved with so-called immunotherapies. The mechanisms of immunoregulation during normal pregnancy are substantially unknown. However, it has been found that a passive immunotherapy in pregnant women with risk of abortion will be successful in 80% of all cases. Polyvalent immunoglobulins are intravenously administered to the women concerned up to about the 25th gestational week. As a rule, the infusions are well tolerated, but slight side effects such as headache, sensation of dizziness or rise in temperature cannot be ruled out during first infusion (Mueller-Eckhardt, G. et al., Beitr Infusionsther. Basel, Karger 26, pp. 298–301, 1990). However, the costs of this therapy during which up to about 150 g immunoglobulins are administered are high.

Another form of immunotherapy is the treatment with allogenic leukocytes, the treatment being most of the time performed twice. The published success rates are between 30% and 80% and seem to be independent of the question whether cells of the partner or of third parties are isolated. According to reports the side effects are small. It should however be noted that leukocyte therapy entails an HLA immunization in most cases, such an immunization being possibly of considerably disadvantage to the women treated in case of a medically necessary organ and/or blood transfusion at a later time (Clark, D. A. and Daya, S., Am. J. Reprod. Immunol. 25, pp. 18–24, 1991).

It is the object of the present invention to provide an inexpensive and well-tolerated drug for treating women with habitual idiopathic abortion to permit normal pregnancy.

This object is attained according to the invention in that at least one hydrolytic enzyme is used for treating the above-mentioned indication.

Surprisingly enough, it has been found that hydrolytic enzymes which have so far predominantly been used for long-term treatment in case of tumors, additional treatment during radiotherapy, support in inflammations and viral infections, rheumatic diseases and circulatory disturbance can be used for preventing another miscarriage in women with habitual idiophatic abortion.

According to the invention both vegetable and animal proteases as well as a combination of vegetable and animal proteases may be used as hydrolytic enzymes. The vegetable proteases bromelain and papain and the animal proteases trypsin and chymotrypsin have turned out to be especially efficient according to the invention.

Bromelain can be isolated from the squeezed juice of pineapple according to conventional methods.

Papain is a proteolytic enzyme which can be made from the milky sap of the unripe, fleshy fruit of the melon tree Carica papaya in conventional methods.

Trypsin and chymotrypsin are proteolytic enzymes which can be obtained from pancreas in a per se known manner.

In addition, rutin (international generic name: rutoside), a glucoside belonging to the flavonoids, may preferably be used.

The use of hydrolytic enzymes according to the invention in combination with gestagens and/or estrogens for supporting pregnancy is especially preferred. Hydroxyprogesterone caproate is above all suited as gestagen, and estradiol valerate as estrogen.

Furthermore, common adjuvants and/or carriers can be used for making pharmaceutical preparations containing the enzymes according to the invention.

An especially good efficiency is attained through the combined use of 20 to 100 mg bromelain, 40 to 120 mg papain, 10 to 60 mg trypsin, 20 to 60 mg chymotrypsin and 50 to 150 mg rutoside×3 $H_2O$ per unit of dose.

The following amounts are preferably used:

a) 100 mg papain, 40 mg trypsin and 40 mg chymotrypsin;

b) 90 mg bromelain, 48 mg trypsin and 100 mg rutoside×3 $H_2O$; or c) 45 mg bromelain, 60 mg papain and 24 mg trypsin.

The following clinical example will explain the invention:

CLINICAL EXAMPLE 12 pregnant women with the indication of habitual idiophatic abortion were treated with the orally administered hydrolytic enzymes papain, trypsin and chymotrypsin. The treatment with two enzyme tablets (Wobe-Mucos® with a content of 100 mg papain, 40 mg trypsin and 40 mg chymotrypsin, three times a day) was commenced before gestational week 12. Estrogen/gestagen (Gravibinon® with a content of 250 mg hydroxyprogesterone caproate and 5 mg estradiol valerate in 1 ml injection solution, initial dose 2 ml/day, treatment dose 1 ml/every second day) were additionally administered.

In all cases pregnancy continued beyond 28 weeks. Neonatal Apgar score was 9–10, delivery weight of the neonate and placental weight were within physiological limits.

The acceptance of the enzyme therapy was high. Side effects were not discovered. The clinical example shows that, surprisingly enough, hydrolytic enzymes can successfully be used for preventing abortion.

We claim:

1. A method for the prophylaxis of a spontaneous abortion in pregnant women in need thereof comprising the administration of at least one hydrolytic enzyme.

2. The method according to claim 1, wherein said hydrolytic enzyme comprises a vegetable protease.

3. The method according to claim 2, wherein said vegetable protease is bromelain or papain.

4. The method according to claim 1, wherein said hydrolytic enzyme comprises an animal protease.

5. The method according to claim 4, wherein said animal protease is trypsin or chymotrypsin.

6. The method according to any one of claims 1-5 further comprising the administration of a glucoside.

7. The method according to claim 6, wherein said glucoside is rutin.

8. The method according to any one of claims 1-5 further comprising the administration of at least one gestagen.

9. The method according to claim 8 further comprising the administration of a glucoside.

10. The method according to claim 8, wherein said gestagen is hydroxyprogesterone caproate.

11. The method according to any one of claims 1-5 further comprising the administration of at least one estrogen.

12. The method according to claim 9 further comprising the administration of at least one estrogen.

13. The method according to claim 12, wherein said estrogen is estradiol valerate.

14. The method according to claim 8 further comprising the administration of at least one estrogen.

* * * * *